(12) United States Patent
Ogden et al.

(10) Patent No.: US 7,189,209 B1
(45) Date of Patent: Mar. 13, 2007

(54) METHOD FOR USING ACOUSTIC SHOCK WAVES IN THE TREATMENT OF A DIABETIC FOOT ULCER OR A PRESSURE SORE

(75) Inventors: John A. Ogden, Atlanta, GA (US); Roy S. Brown, Lawrenceville, GA (US); Argil Wheelock, Lookout Mountain, TN (US)

(73) Assignee: Sanuwave, Inc., Marietta, GA (US)

( * ) Notice: Subject to any disclaimer, the term of this patent is extended or adjusted under 35 U.S.C. 154(b) by 168 days.

(21) Appl. No.: 10/246,264

(22) Filed: Sep. 18, 2002

Related U.S. Application Data

(60) Continuation-in-part of application No. 09/427,686, filed on Dec. 23, 1998, now abandoned, which is a division of application No. 08/799,585, filed on Feb. 12, 1997, now abandoned.

(60) Provisional application No. 60/014,742, filed on Mar. 29, 1996.

(51) Int. Cl.
*A61N 7/00* (2006.01)

(52) U.S. Cl. .......................................... 601/2; 600/427

(58) Field of Classification Search ................ 600/427, 600/439; 601/2–4
See application file for complete search history.

(56) References Cited

U.S. PATENT DOCUMENTS

| | | | |
|---|---|---|---|
| 2,559,227 A | 7/1951 | Rieber ......................... 128/24 |
| 3,499,437 A | 3/1970 | Balamuth ..................... 128/24 |
| 3,776,223 A | 12/1973 | Yeager et al. ................. 128/66 |
| 3,942,531 A | 3/1976 | Hoff et al. .................... 128/328 |
| 4,526,168 A | 7/1985 | Hassler et al. |
| 4,530,360 A | 7/1985 | Duarte ........................ 128/419 |
| 4,610,249 A | 9/1986 | Makofski et al. |
| 4,630,607 A | 12/1986 | Duinker et al. |
| 4,669,472 A | 6/1987 | Eisenmenger ................ 128/328 |
| 4,671,254 A | 6/1987 | Fair |
| 4,721,108 A | 1/1988 | Heine et al. |
| 4,802,525 A | 2/1989 | Heine et al. .................... 164/48 |
| 4,805,600 A | 2/1989 | Wess et al. ................. 128/24 A |
| 4,807,627 A | 2/1989 | Eisenmenger ................ 128/328 |
| 4,809,682 A | 3/1989 | Forssmann et al. ........... 128/24 |
| 4,844,079 A | 7/1989 | Naser et al. |
| 4,887,600 A | 12/1989 | Watson et al. ............... 606/128 |
| 4,896,673 A | 1/1990 | Rose et al. ............. 128/660.03 |
| 4,905,671 A | 3/1990 | Senge et al. ................... 128/24 |
| 4,905,672 A | 3/1990 | Schwarze et al. ......... 128/24 A |
| 4,924,858 A | 5/1990 | Katona ........................ 128/24 |

(Continued)

FOREIGN PATENT DOCUMENTS

DE 32 20 751 A1 12/1983

(Continued)

OTHER PUBLICATIONS

Dahmen, G.P. et al., "Extracorporeal Shock Wave Therapy in the Area of Bones, Specifically Soft Tissue Area of the Shoulder," *Extracta Orthopaedica*, vol. 15, No. 11, pp. 25-27, 1992.

(Continued)

*Primary Examiner*—Ruth S. Smith
(74) *Attorney, Agent, or Firm*—Smith, Gambrell & Russell, LLP

(57) ABSTRACT

A method of treating pathological conditions associated with bone and musculoskeletal environments and soft tissues involves applying acoustic shock waves to cause localized trauma, including micro-disruptions, non-osseous tissue stimulation, increased vascularization, and circulation and induction of growth factors to induce or accelerate the body's natural healing processes and responses.

11 Claims, 2 Drawing Sheets

U.S. PATENT DOCUMENTS

| | | |
|---|---|---|
| 4,928,672 A | 5/1990 | Grasser et al. |
| 4,938,232 A | 7/1990 | Wess et al. ............... 128/802 |
| 4,940,050 A | 7/1990 | Forssmann et al. ....... 128/24 A |
| 4,979,501 A | 12/1990 | Valchanov et al. ........... 128/24 |
| 4,998,528 A | 3/1991 | Erhardt .................... 128/24 A |
| 5,047,685 A | 9/1991 | Nowacki et al. |
| 5,058,569 A | 10/1991 | Hassler et al. |
| 5,070,861 A | 12/1991 | Einars et al. ......... 128/24 OEL |
| 5,071,422 A | 12/1991 | Watson et al. .............. 606/128 |
| 5,072,721 A | 12/1991 | Weiler et al. ........... 128/24 EL |
| 5,072,733 A | 12/1991 | Spector et al. |
| 5,078,124 A | 1/1992 | Viebach et al. ....... 128/24 OEL |
| 5,119,801 A | 6/1992 | Eizenhoefer et al. ... 128/24 EL |
| 5,137,014 A | 8/1992 | Boehm .................... 128/24 EL |
| 5,152,289 A | 10/1992 | Viebach et al. ........ 128/660.03 |
| 5,152,767 A | 10/1992 | Sypal et al. |
| 5,172,692 A | 12/1992 | Kulow et al. .................. 128/24 |
| 5,174,280 A | 12/1992 | Gruenwald et al. ..... 128/24 EL |
| 5,176,675 A | 1/1993 | Watson et al. ................. 606/15 |
| 5,178,135 A | 1/1993 | Uchiyama et al. .......... 128/240 |
| 5,178,136 A | 1/1993 | Wess et al. .................... 128/24 |
| 5,181,512 A | 1/1993 | Viebach et al. ........ 128/660.03 |
| 5,191,560 A | 3/1993 | Lobentanzer et al. ....... 362/175 |
| 5,191,880 A | 3/1993 | McLeod et al. .............. 128/24 |
| 5,195,508 A | 3/1993 | Müller et al. ........... 128/24 EL |
| 5,199,420 A | 4/1993 | Artmeier ................ 128/24 EL |
| 5,207,215 A | 5/1993 | Rattner et al. |
| 5,209,222 A | 5/1993 | Viebach et al. ....... 128/24 OEL |
| 5,211,160 A | 5/1993 | Talish et al. .................. 128/24 |
| 5,222,483 A | 6/1993 | Plisek |
| 5,222,484 A | 6/1993 | Krauss et al. |
| 5,224,468 A | 7/1993 | Grünewald et al. ........... 128/24 |
| 5,228,447 A | 7/1993 | Harder et al. |
| 5,230,328 A | 7/1993 | Buchholtz et al. |
| 5,231,976 A | 8/1993 | Wiksell ........................ 128/24 |
| 5,240,000 A | 8/1993 | Herrmann et al. ..... 128/653.01 |
| 5,240,005 A | 8/1993 | Viebach ................. 128/663.01 |
| 5,247,924 A | 9/1993 | Suzuki et al. |
| 5,251,630 A | 10/1993 | Rattner |
| 5,259,368 A | 11/1993 | Wiksell |
| 5,259,384 A | 11/1993 | Kaufman et al. ......... 128/660.1 |
| 5,269,306 A | 12/1993 | Warnking et al. ...... 128/660.03 |
| 5,279,282 A | 1/1994 | Oppelt |
| 5,284,143 A | 2/1994 | Rattner .................... 128/653.1 |
| 5,287,856 A | 2/1994 | Treiber .................. 128/660.03 |
| 5,301,659 A | 4/1994 | Brisson et al. |
| 5,305,731 A | 4/1994 | Buccholtz |
| 5,309,898 A | 5/1994 | Kaufman et al. .............. 601/2 |
| 5,316,000 A | 5/1994 | Chapelon et al. ...... 128/660.03 |
| 5,327,890 A | 7/1994 | Matura et al. ........... 128/653.1 |
| 5,329,928 A | 7/1994 | Brisson et al. |
| 5,347,997 A | 9/1994 | Weiler et al. .................. 601/3 |
| 5,374,236 A | 12/1994 | Hassler .......................... 601/2 |
| 5,393,296 A | 2/1995 | Rattner .......................... 601/4 |
| 5,409,446 A | 4/1995 | Rattner .......................... 601/4 |
| 5,419,327 A | 5/1995 | Rohwedder et al. ... 128/660.03 |
| 5,431,641 A | 7/1995 | Grözinger et al. .......... 604/283 |
| 5,435,304 A | 7/1995 | Oppelt et al. |
| 5,450,848 A | 9/1995 | Okazaki et al. |
| 5,458,130 A | 10/1995 | Kaufman et al. ...... 128/661.01 |
| 5,458,652 A | 10/1995 | Uebelacker .................... 601/4 |
| 5,505,729 A | 4/1996 | Rau ............................ 606/40 |
| 5,524,620 A | 6/1996 | Rosenschein ............ 128/653.1 |
| 5,545,124 A | 8/1996 | Krause et al. .................. 601/2 |
| 5,595,178 A * | 1/1997 | Voss et al. ................... 600/427 |
| 5,688,263 A | 11/1997 | Hauptmann et al. .......... 606/13 |
| 5,692,509 A | 12/1997 | Voss et al. ............... 128/653.1 |
| 5,720,762 A | 2/1998 | Bass .......................... 606/192 |
| 5,727,556 A | 3/1998 | Weth et al. ............ 128/660.03 |
| 5,810,748 A | 9/1998 | Ueberle .......................... 601/4 |
| 5,921,930 A | 7/1999 | Überle ....................... 600/439 |
| 5,941,838 A | 8/1999 | Eizenhöfer ..................... 601/2 |
| 6,066,123 A | 5/2000 | Li et al. ...................... 604/507 |
| 6,113,560 A | 9/2000 | Simnacher ..................... 601/4 |
| 6,186,963 B1 | 2/2001 | Schwarze et al. .............. 601/2 |
| 6,190,336 B1 | 2/2001 | Duarte et al. .................. 601/2 |
| 6,298,264 B1 | 10/2001 | Zhong et al. |
| 6,325,769 B1 | 12/2001 | Klopotek |
| 6,368,292 B1 | 4/2002 | Ogden et al. |
| 6,390,995 B1 | 5/2002 | Ogden et al. |
| 6,461,305 B1 | 10/2002 | Schnall |
| 6,488,633 B1 | 12/2002 | Schnall |
| 6,599,299 B2 | 7/2003 | Schultz |
| 6,679,179 B1 | 1/2004 | Bohl et al. |
| 6,755,821 B1 | 6/2004 | Fry |
| 6,780,161 B2 | 8/2004 | Faragalla et al. |
| 6,850,465 B2 | 2/2005 | Rohwedder |
| 6,869,407 B2 | 3/2005 | Ein-Gal |
| 2002/0002345 A1 | 1/2002 | Marlinghaus |
| 2003/0050559 A1 | 3/2003 | Ein-Gal |
| 2003/0060738 A1 | 3/2003 | Ein-gal |
| 2003/0129154 A1* | 7/2003 | McDaniel .................. 424/70.1 |
| 2003/0149359 A1 | 8/2003 | Smith |
| 2004/0116787 A1 | 6/2004 | Schnall |

FOREIGN PATENT DOCUMENTS

| | | |
|---|---|---|
| DE | 37 09 404 C2 | 11/1988 |
| DE | 4036981 | 5/1992 |
| DE | 43 15 282 C2 | 11/1994 |
| DE | 19718513 | 5/1998 |
| DE | 19718512 | 6/1998 |
| DE | 197 46 321 A1 | 4/1999 |
| EP | 0 324 711 | 7/1989 |
| EP | 0324163 | 7/1989 |
| EP | 0324711 A2 | 7/1989 |
| EP | 0450423 | 1/1997 |
| FR | 2447186 A | 8/1980 |
| WO | WO 96/09621 | 3/1996 |
| WO | WO 2005/075020 A1 | 8/2005 |

OTHER PUBLICATIONS

Guerkov, H., Pulsed Electromagnetic Fields Increase Growth Factor Release by Nonunion Cells, *Clinical Orthopaedics and Related Research*, No. 384, pp. 265-279, 2001.

Almekinders, Louis C., "Tendinitis and Other Chronic Tendinopathies," *Journal of the American Academy of Orthopaedic Surgeons*, May/Jun. 1998, vol. 6, No. 3, pp. 157-164.

Nakano, Kenneth K., "Peripheral nerve entrapments, repitive strain disorder, occupation-related syndromes, bursitis, and tendonitis," *Current Opinion in Rheumatology*, 1991, vol. 3, No. 2, pp. 226-239.

Stell, Ian M., "Management of acute bursitis: outcome study of a structured approach," *Journal of the Royal Society of Medicine*, Oct. 1999, vol. 92, No. 10, pp. 516-521.

Maffulli, Nicola et al., "Overuse Tendon Conditions: Time to Change a Confusing Terminology," *Arthroscopy: The Journal of Arthroscopic & Related Surgery*, Nov./Dec. 1998, vol. 14, No. 8, pp. 840-843.

Dahman, G.P. et al., "Extracorporeal Shock Wave Therapy (ESWT) for the Treatment of Pains in Soft Tissues Near the Bone: Indication, Technique, and Preliminary Results," in Attempto Medizin und Technik. Jg. 1993. S. 143 bis 148 Attempto Verlag Tübingen GmBH (including English translation thereof).

Final Programme and Abstracts, European Society for Musculoskeletal Shockwave Therapy (ESMST) 2nd International Congress, May 27-29, 1999, London, England.

Lin, Jian-Hao et al., "Temporal expression of nitric oxide synthase isoforms in healing Achilles tendon," *Journal of Orthopaedic Research*, No. 19 (2001), pp. 136-142.

Ogden, John A, et al., "Principles of Shock Wave Therapy," *Clinical Orthopaedics and Related Research*, Jun. 2001, No. 387, pp. 8-17.

Ogden, John A, et al., "Shock Wave Therapy for Chronic Proximal Plantar Fasciitis," *Clinical Orthopaedics and Related Research*, Jun. 2001, No. 387, pp. 47-59.

Schmitt, J. et al., "Die extrakorporale Stoβwellen-therapie (ESWT) als therapeutische Option beim Supraspinatussehnensyndrom? (English: ESWT as a therapeutic option for supraspinatus tendonitis? Results of a placebo-controlled clinical trial after one year")", Der Orthopäde, vol. 31, pp. 652-657, 2002 (English Abstract—p. 653).

Eisenmenger, W., "The Mechanisms of Stone Fragmentation in ESWL," *Ultrasound in Med. & Biol.*, vol. 27, No. 5, pp. 683-691, 2001.

Eisenmenger, W. et al., "The First Clinical Results of 'Wide-Focus and Low-Pressure' ESWL," *Ultrasound in Med. & Biol.* vol. 28, No. 6, pp. 769-774, 2002.

Delius, M. "Biological effects of shock waves—more than "just" lithotripsy" Zentralbl. Chir., 1995, vol. 120, pp. 259-273.

Jianming Song, et al., "Combined Shock-Wave and Immunogene Therapy of Mouse Melanoma and Renal Carcinoma Tumors," Ultrasound in Med. & Biol., 2002, pp. 957-964, vol. 28, No. 7.

L. Perlick, et al., "Extracoporal shock wave treatment on the Achilles tendonitis: Experimental and preliminary clinical results," Z. Orthop, 2002, pp. 275-280, vol. 140. No. 3.

C.A. Speed, "Extracorporeal shock wave therapy for plantar fasciitis. A double blind randomized controlled trial," Journal of Orthopedic Research, 2003, pp. 937-940, vol. 21, Orthopedic Research Society.

W. Schaden, et al., "Extracorporeal Shockwave Therapy for Chronic Skin Lesions," 8th International Congress of the International Society Musculoskeletal Shockwave Therapy, May 29-Jun. 1, 2005.

Ludger Gerdesmeyer, et al., "Antibacterial Effects of Extracorporeal Shock Waves," Ultrasound in Med. & Biol., 2005, pp. 115-119, vol. 31, No. 1, World Federation for Ultrasound in Medicine & Biology.

Meirer R., et al., "Extracorporeal Shock Wave May Enhance Skin Flap Survival in an Animal Model," The British Association of Plastic Surgeons, 2005, pp. 53-57, vol. 58.

Huemer GM., et al., "Comparison of the effectiveness of gene therapy with transforming growth factor-beta or extracorporal shock wave therapy to reduce ischemic necrosis in an epigastric skin flap model in rats," Wound Repair Regen., May-Jun. 2005, pp. 262-268, vol. 13, No. 3.

R. Meirer, et al., "Shock wave therapy: An innovative treatment method for partial thickness burns," Burns, 2005.

Georg M. Huemer, et al., "Adenovirus-Mediated Transforming Growth Factor-β Ameliorates Ischemic Necrosis of Epigastric Skin Flap in Rat Model," 2003, pp. 1-20.

Ching-Jen Wang, "Shock Wave-Enhanced Neovascularization at the Tendon-Bone Junction: An Experiment in Dogs," The Journal of Foot & Ankle Surgery, Jan./Feb. 2002, pp. 16-22, vol. 41, No. 1.

W. Boxberg, "Shockwave treatment for refractory soft-tissue pain," Der Chirung, 1996.

* cited by examiner

METHOD FOR USING ACOUSTIC SHOCK WAVES IN THE TREATMENT OF A DIABETIC FOOT ULCER OR A PRESSURE SORE

This application is a continuation-in-part application of U.S. application Ser. No. 09/427,686, filed Dec. 23, 1998, now abandoned, which is a divisional of U.S. application Ser. No. 08/799,585, filed Feb. 12, 1997, now abandoned, which claims priority to U.S. Provisional Application No. 60/014,742, filed Mar. 29, 1996, now abandoned, the entire contents of each of which are hereby incorporated by reference.

FIELD OF THE INVENTION

This invention relates to a method for medical treatment of pathological conditions. More particularly, the invention relates to a method for using acoustic shock waves to treat a variety of pathological conditions associated with bone and musculoskeletal environments (including bone, cartilage, ligaments, tendons, fascia, joint capsules, bone marrow and muscle) such as cutaneous, subcutaneous, and fascial geographic tissue injuries, defects, or deficits; degenerative joint diseases; soft tissue injuries; decalcification; osteochondromatosis and enchondromatosis; facet osteoarthritis; abnormal neuromuscular pain; and abnormalities of development.

BACKGROUND OF THE INVENTION

Inventors have recognized the effectiveness of the use of energy wave forms for medical treatment of various pathologies. Extracorporeal shock wave therapy (ESWT) is the non-surgical treatment of medical conditions using acoustic shock waves. Lithotripsy, the use of shock waves to fragment kidney stones, was introduced in Europe in the early 1980s, and by the mid-1980s shock wave lithotripsy had been established worldwide as the treatment of choice for disintegrating kidney stones. In 1986, European researchers conducted animal experiments which revealed that shock waves have the potential to stimulate bone formation by activation of osteoblast cells. The first positive results were reported after application of shock waves to artificial humerus fractures in rats. Since then, further experimentation with shock waves for other medical uses has continued, and today shock wave therapy has become an accepted method of treatment for a number of orthopedic indications. This method of treatment is increasingly popular with patients and physicians alike because it provides a non-surgical, non-invasive alternative for patients.

A shock wave is a type of acoustic energy resulting from phenomena, such as an explosion or lightning, that create a sudden intense change in pressure. The intense changes in pressure produce strong waves of energy that can travel through any elastic medium such as air, water, human soft tissue, or certain solid substances such as bone. Early approaches of using shock waves for medical treatment required immersing the patient in water and directing a shock wave, generated by an underwater spark discharge, at a solid site to be treated, such as a bone or kidney stone. When the shock wave hits the solid site, a liberation of energy from the change of acoustic impedance from water to the solid site produces pressure in the immediate vicinity of the site.

Three methods are currently used to create the acoustic shock waves for ESWT: (1) electrohydraulic, or spark gap; (2) electromagnetic, or EMSE; and (3) piezoelectric. Each is based upon its own unique physical principles. Spark gap systems incorporate an electrode (spark plug) to initiate a shock wave and ellipsoid to focus it. EMSE systems utilize an electromagnetic coil and an opposing metal membrane. Piezoelectric systems form acoustical waves by mounting piezoelectric crystals to a spherical surface.

In general, spark gap systems deliver the same level of energy as other methods produce, but over a broader area, and therefore deliver a greater amount of positive shock wave energy to targeted tissue. In spark gap systems, high energy shock waves are generated when electricity is applied to an electrode positioned in an ellipsoid immersed in treated water. When the electrical charge is fired, a small amount of water is vaporized at the tip of the electrode and a shock wave is produced. The shock wave ricochets from the side of an ellipsoid and converges at a focal point, which is the location of the area to be treated. Treatment areas are typically localized either by palpation or through the use of a fluoroscopy device.

The use of energy wave forms for medical treatment of various bone pathologies is known in the art. Some prior systems use ultrasound transducers, in direct contact with the skin of the patient, for transmitting ultrasound pulses to the site of the bone defect. Other devices utilize piezoelectric materials fastened adjacent to the pathological site on the patient's limb to produce ultrasonic energy in the vicinity of the bone pathology for administering therapy.

U.S. Pat. No. 4,905,671 to Senge et al. ("Senge"), issued on Mar. 6, 1990, teaches a method of applying acoustic shock waves to induce bone formation. Senge teaches that the acoustical sound waves previously used for treatment of bone have a generally damped sinusoidal wave form centered on ambient pressure. Senge differentiates an idealized shock wave from such acoustical sound waves in that the shock wave has a single pressure spike with a very steep onset, a more gradual relaxation, and virtually no oscillation to produce acoustic tension.

Senge utilizes the extremely short rise time of the shock wave to create high compression zones within bone tissue to cause restrictions of the microcompartments of the bone. Senge purports that such restrictions cause the formation of hematomas within bone, which in turn, induce the formation of new bone. Senge utilizes a shock wave source consisting of a spark gap between electrodes within a container of water. A metallic, ellipsoid-shaped structure surrounds a rear portion of the spark gap, opposite the patient, to produce a known focal point for positioning within the patient's pathological bone site. This device also requires that the patient be submerged in the water.

U.S. Pat. No. 4,979,501 to Valchanov et al. ("Valchanov"), issued on Dec. 25, 1990, teaches a method and apparatus for treating bone pathologies with shock or "impact" waves for correction of delayed bone consolidation and bone deformations. The method disclosed in Valchanov includes treating the affected bone site once or consecutively for a period of 10–120 minutes and subsequently immobilizing the limb for a period from 15 to 90 days. The impact wave generating device disclosed by Valchanov generally consists of a vessel which contains a transmitting medium or acoustic liquid such as water contained therein. At a bottom portion of the vessel are opposed electrodes which are adapted to produce a shock across the gap. Therefore, the patient is not submerged for treatment.

Other references, including U.S. Pat. Nos. 5,284,143, 5,327,890, 5,393,296, 5,409,446, and 5,419,327, teach the treatment of bone pathologies utilizing shock wave therapy in combination with imaging means for localizing the pathology during treatment. Still other devices utilize transducers for producing ultrasonic waves for therapy of soft tissue. These past methods for treating soft tissue surrounding bone utilized a transducer for the generation of ultrasonic waves for wave propagation into the pathological site within the soft tissue area. Furthermore, as described by Senge, clinicians traditionally implemented shock wave therapy for the treatment of bone.

Therefore, what is needed is a rapid, time-restricted and effective shock wave therapy treatment for pathological conditions not only associated with bones, but also bone and musculoskeletal environments and soft tissue.

SUMMARY OF THE INVENTION

The present invention relates to methods for treating pathological conditions associated with bones and musculoskeletal environments, as well as soft tissue. More specifically, certain exemplary embodiments of the present invention include applying acoustic shock waves to the site of a pathological condition associated with bone, a musculoskeletal environment, or soft tissue to induce, reactivate, or accelerate the body's natural healing processes. Certain exemplary embodiments may include the steps of locating the site of a pathological condition, generating acoustic shock waves, focusing the acoustic shock waves on the pathological site, and applying the focused acoustic shock waves to the site to induce localized trauma or micro-injury and increased vascularization.

According to an embodiment of the present invention, acoustic shock waves are used to treat a variety of pathological conditions associated with bone and musculoskeletal environments and soft tissue, such as cutaneous, subcutaneous, and fascial geographic tissue injuries, defects, or deficits and degenerative joint diseases, including osteoporosis, osteomalacia, and arthritis. For the purposes of this specification, the musculoskeletal environment may include the cartilage, tendons, ligaments, joint capsules, fascia, and muscles which functionally support skeletal structures.

In further embodiments of the present invention, exemplary methods may promote fusion in partially ankylosed joints and reabsorption of heterotopic calcifications and ossifications. Soft tissue injuries may be treated, including damaged rotator cuffs, impingement syndrome, and tendonopathies. Additional pathologies that respond positively to certain exemplary embodiments of the present invention include sacroiliac pain, osteochondromatosis and enchondromatosis, facet osteoarthritis, focal reflex dystrophy pain, phantom pain, and non-adaptive bone disease and fatigue failure in equines and canines.

Some methods according to the present invention may also affect bone growth. Specifically, application of acoustic shock waves may induce early closure of the growth plate (epiphyseodesis) and osteogenesis at margins of vascularized bone transplants or transport bone in bone lengthening. Certain exemplary embodiments of the invention may also promote stimulation of bone formation and vascular ingrowth in bone lengthening and vascularized bone grafting.

Physical palpation, X-ray image intensification, or ultrasonography may be used to precisely locate the pathological site. Once the site is located, certain embodiments may utilize a spark gap generator to generate acoustic shock waves and an ellipsoid reflector or focusing lens to specifically direct the acoustic shock waves to the impact (treatment) site. Other objects and features of the present invention will be more readily understood from the following detailed description.

DETAILED DESCRIPTION OF THE INVENTION

Certain exemplary embodiments of the present invention require the use of a locating device or palpation to locate the site or suspected site of the pathological condition. Locating devices may include, but are not limited to X-ray or ultrasound machines. For example, the method and apparatus described in U.S. Pat. No. 4,896,673 to Rose et al., issued Jan. 30, 1990, the disclosure of which is incorporated herein by reference in its entirety, may locate the site or suspected site of the pathological condition.

Certain exemplary embodiments of methods according to the invention require a shock wave source such as a spark gap generator, such as the ones described in U.S. Pat. No. 4,905,671 to Senge et al.; U.S. Pat. No. 4,979,501 to Valchanov et al.; U.S. Pat. No. 5,284,143 to Rattner; U.S. Pat. No. 5,327,890 to Matura et al.; U.S. Pat. No. 5,393,296 to Rattner; U.S. Pat. No. 5,409,446 to Rattner; and U.S. Pat. No. 5,419,327 to Rohwedder et al., the disclosures of each of which are hereby incorporated by reference in their entirety. Other exemplary embodiments may utilize the electromagnetic shock wave source and parabolic wave focusing means of the type described in U.S. Pat. No. 5,327,890 to Matura et al., the disclosure of which is incorporated herein by reference in its entirety. The focusing means may also comprise parabolic reflectors such as those commonly utilized in kidney lithotripters.

Figure 1:
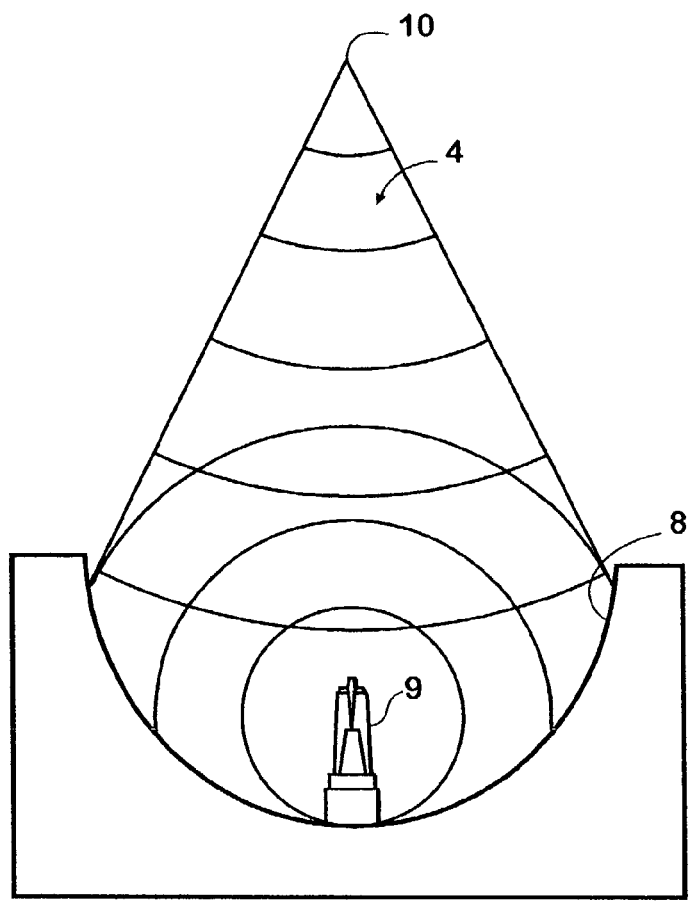
FIG. 1 is a schematic representation of a shock wave generation device with a focusing mechanism used in accordance with the inventive method.

Certain exemplary embodiments of the invention also require means for focusing the acoustic shock waves with an appropriate device, such as an ellipsoid reflector or parabolic focusing lens. The reflector is generally located in a therapy head, which directs the waves to a focal point. FIG. 1 is a schematic representation of such a shock wave generator and focusing means. Shock waves 4 radiate from an electrode 9 and through water (not shown). Waves 4 reflect from an ellipsoid surface 8 and toward a focal point 10.

Figure 2:
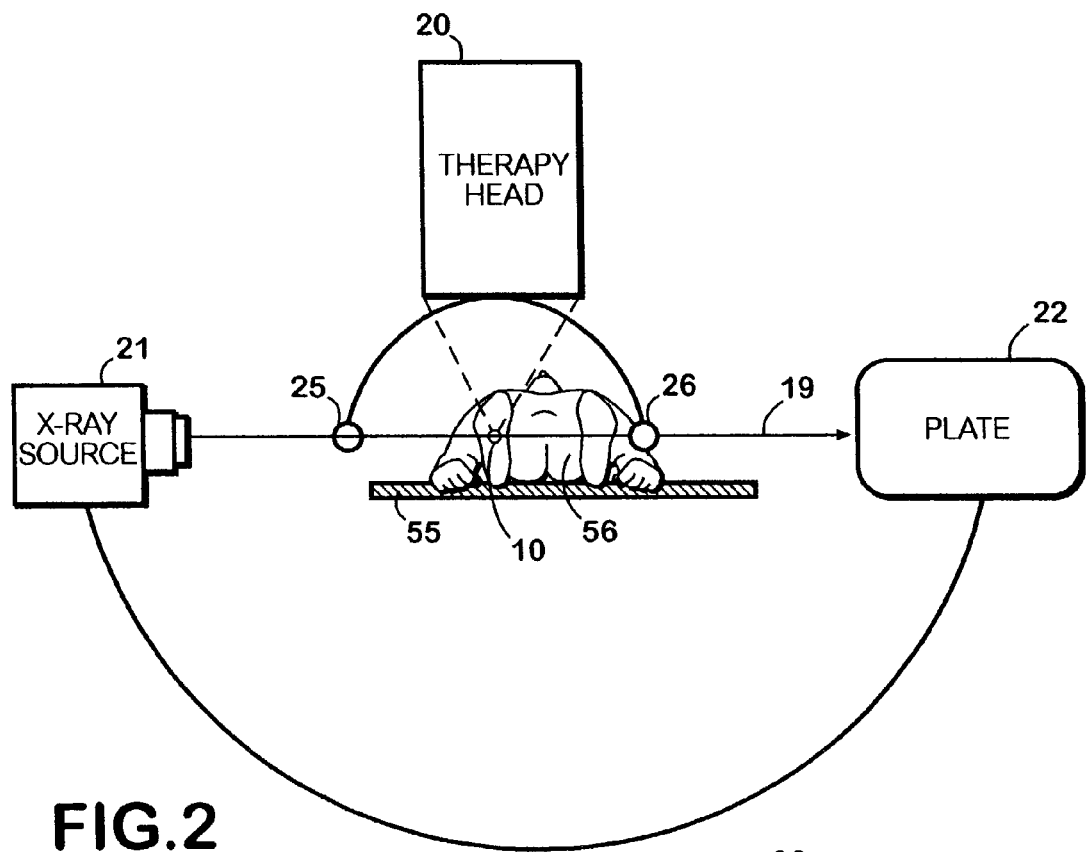
FIG. 2 is a schematic representation of a therapy head and locating mechanism used in accordance with the inventive method.
Figure 3:
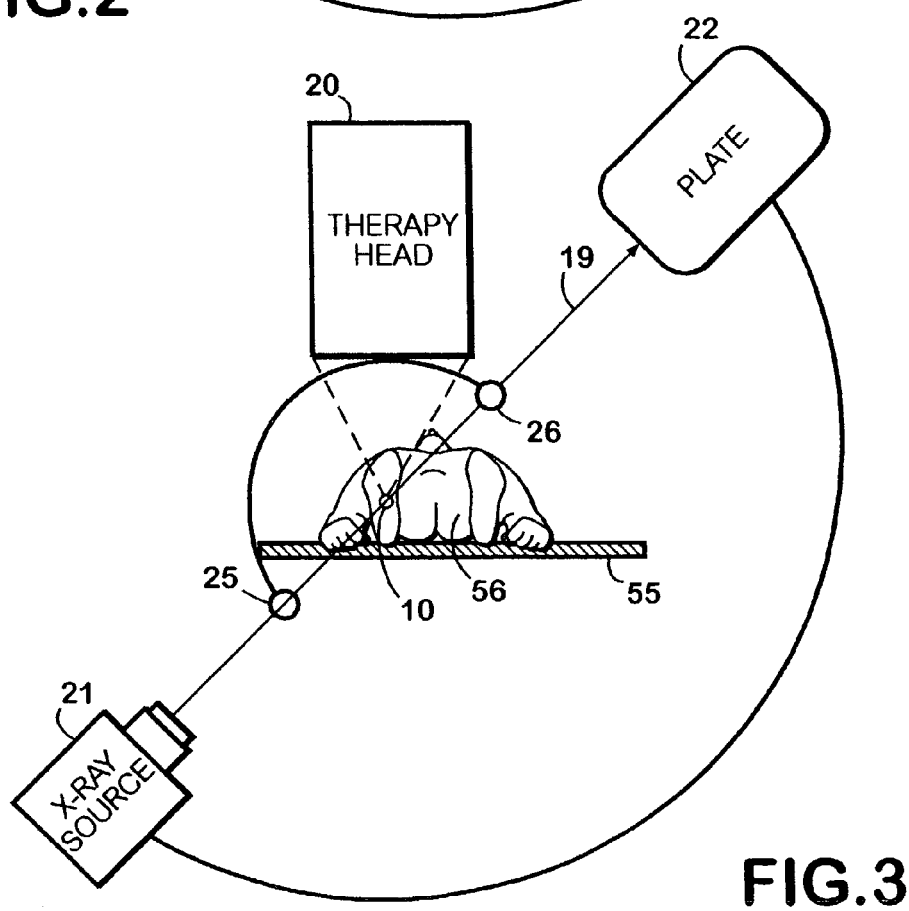
FIG. 3 is a schematic representation of the therapy head and locating mechanism of FIG. 2 with the locating mechanism situated at a 45 degree angle with respect to a horizontal plane.

In an exemplary embodiment, the therapy head also includes a targeting device which functions in conjunction with an X-ray machine locating device, as is illustrated in FIGS. 2 and 3. FIGS. 2 and 3 schematically illustrate a patient 56 positioned on a surface 55 during a treatment session. Two movable targets 25 and 26 are connected mechanically to a therapy head 20 so that the pair of targets 25 and 26 may rotate around at least two different axes with an imaginary connecting line 19. An X-ray source 21 and a plate 22 define a connecting line 19 which passes through targets 25 and 26. Connecting line 19 always extends between the two targets and through focal point 10 of the shock waves.

Figure 4:
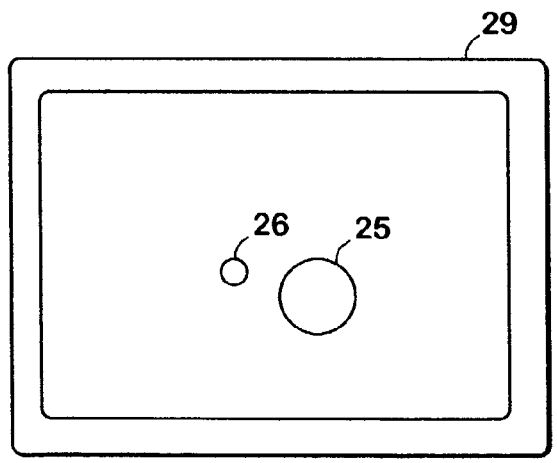
FIGS. 4 and 5 illustrate schematic representations of monitors that display images of alignment targets for the therapy head in unaligned and aligned positions, respectively.
Figure 5:
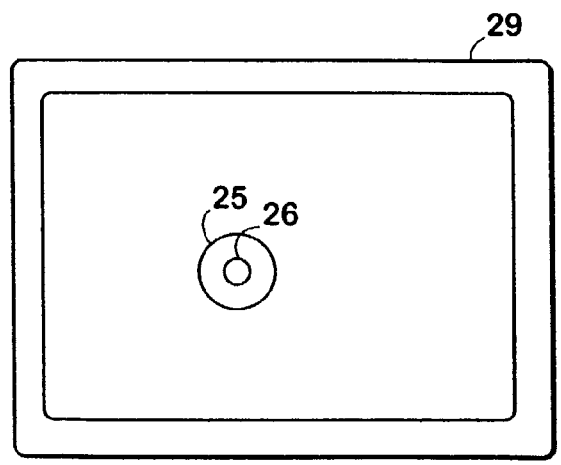

Before beginning treatment in accordance with certain exemplary embodiments of the present invention, the clinician aligns the tissue area to be treated with the approximate center of an X-ray image being projected by source 21. An appropriate monitor 29 illustrates the projection of the X-ray image as illustrated in FIGS. 4 and 5. As illustrated in FIG. 4, when targets 25 and 26 do not coincide with one another, then focal point 10 is not aligned with the treatment site. After proper alignment, as shown in FIG. 5, targets 25 and 26 coincide with the treatment site, and the clinician may begin treatment. As illustrated in FIG. 3, the imaging mechanism may also be positioned at various angles with respect to the patient depending on the location of the treatment site within the patient. Alternatively, an ultrasound locating unit positions the shock wave focal point between the patient's pathological site and the acoustically reflective object.

Certain exemplary embodiments of the present invention include methods of applying acoustic shock waves to the site of a pathological condition associated with bone, a musculoskeletal environment, or soft tissue to induce, reactivate, or accelerate the body's natural healing processes, especially through natural cellular and molecular (macromolecular) biologic responses, including the stimulation of tissue specific group factors (cytokines, morphogenic proteins), and to improve local microcirculation through activated neoangiogenesis.

Certain exemplary embodiments of the present invention may further include locating the site or suspected site of a pathological condition, generating acoustic shock waves, focusing the acoustic shock waves on the located site, and applying the focused acoustic shock waves to the site to induce localized trauma and cellular apotosis therein, including micro-fractures, as well as to induce osteoblastic responses such as cellular recruitment, stimulate formation of molecular bone, cartilage, tendon, fascia, and soft tissue morphogens and growth factors, and to induce vascular neoangiogenesis. Application of acoustic shock waves similarly induces neoangiogenesis in musculoskeletal environment tissues and the formation, recruitment, or stimulation of tissue specific morphogenetic macromolecules and growth factors.

Micro-disruptions resulting from the shock wave therapy induce disruption of small blood vessels (capillaries), cellular changes, and extracellular matrix and macromolecular changes in a controlled fashion for the purpose of stimulating increased neoangiogenesis leading to adequate revascularization in ischemic tissues. The increased circulation and revascularization then induce the body's natural cellular (tissue specific) healing processes. The accompanying cellular changes lead to or are associated with elaboration and production of bone and tissue morphogenetic proteins, known as growth factors, as well as elaboration and production of nitric oxide synthase isoforms.

Applicants have found unexpected success in the treatment of soft tissue and cancellous bone pathologies using acoustic shock wave therapy. Particular applications of shock wave therapy are illustrated in the following example studies, which include patients that did not significantly respond to conventional treatments for the particular pathology treated.

EXAMPLE 1

Acoustic shock waves were used to treat calcified tendinitis, wherein the affected tendon is inflamed and has developed deposits of calcium salts. A tendon, which is the fibrous corridor band that connects a muscle to a bone or other structure, consists of very densely arranged, almost parallel collagenous fibers, rows of elongated tendon cells, and a ground substance. The tendon may become calcified, stiff, and inflamed. Table 1 below sets out results of acoustic shock wave therapy for the treatment of calcific tendinitis:

TABLE 1

Preliminary Clinical Results For Treatment of Calcific Tendinitis using Acoustic Shock Waves

| | | |
|---|---|---|
| Number of patients: | | 684 |
| Success Rate: | total | 81% |
| | single treatment: | 62% |
| | double treatment: | 19% |
| Shocks Per Treatment: | average: | 750 |
| | min: | 300 |
| | max: | 2500 |
| Energy Applied Per Pulse: | average: | 16 kV |
| | min: | 14 kV |
| | max: | 18 kV |
| Pulse Frequency: | average: | 0.5–4.0 Hz |
| Treatment Duration | average: | 20–30 minutes |
| Anesthesia: | local | |
| Side Effects: | petechial bleedings | |
| History: | Time of prior conventional therapies: | |
| | average: 15 months | |
| | min: 6 months | |
| | max: 12 years | |
| | Prior treatment: Resistant to conventional methods | |
| | Hospitalization: Outpatient | |
| | Follow-up: 3–6 months | |

The treatment included 684 patients with calcific tendinitis with an average success rate of 81%. Of the total number of treated patients, 62% of the patients had a successful recovery after one session, and 19% had a successful recovery after two sessions of acoustic shock wave therapy. An average of 750 shocks per treatment were applied with the minimum being 300 and the maximum being 2500.

The average amount of energy applied for each shock wave pulse was 16 kilovolts with a session minimum of 14 kilovolts and a session maximum of 18 kilovolts. The treatment included local anesthesia, and the side effects of the treatment included petechial bleedings, which are minute hemorrhagic spots approximately the size of pin points on the patient's skin surface, in the vicinity of the treatment site. These resolve within 48 hours with no permanent consequences.

As explained above, each of the patients chosen for this study had not responded to previous conventional therapy. Of the total number of patients treated using acoustic shock wave therapy for calcific tendinitis, the average time for conventional treatment period was 15 months with no response. The maximum prior conventional prior treatment period was 12 years. The minimum prior treatment period for the group of patients was 6 months. Each patient received the shock wave therapy on an outpatient basis, and follow up examinations after 3–6 months for each patient yielded no recurrence of the condition.

EXAMPLE 2

Acoustic shock wave therapy also proves successful in the treatment of epicondylitis. Epicondylitis refers to a condition which may necessitate the removal of an inflamed or diseased external condyle from an elongated bone or the release or repair of attached tendons and fascia. The epicondyle is generally a projection from an elongated bone near its articular extremity. Table 2 summarizes the results of acoustic shock wave treatment on patients suffering from epicondylitis at the elbow.

TABLE 2

Preliminary Clinical Results For Treatment of Epicondylitis Using Acoustic Shock Waves

| | | |
|---|---|---|
| Number of patients: | | 285 |
| Success Rate: | total | 69% |
| | single treatment: | 47% |
| | double treatment: | 22% |
| Shocks Per Treatment: | average: | 780 |
| | min: | 400 |
| | max: | 1500 |
| Energy Applied Per Pulse: | average: | 15 kV |
| | min: | 14 kV |
| | max: | 16 kV |
| Pulse Frequency: | average: | 0.5–4.0 Hz |
| Treatment Duration | average: | 20–30 minutes |
| Anesthesia: | local plexus | |
| Side Effects: | petechial bleedings, post-treatment pain | |
| History: | Time of prior conventional therapies: | |
| | average: 13 months | |
| | min: 4 months | |
| | max: 48 months | |
| | Prior treatment: Resistant to conventional methods | |
| | Hospitalization: Outpatient | |
| | Follow-up: 3–6 months | |

This study included 285 patients treated with an average success rate of 69%. The average success rate consisted of a sum of 47% of the treated patients receiving a single treatment and 22% of the treated patients receiving a double treatment. Each treatment employed an average number of shocks applied per session of 780, with the minimum being 400 and the maximum being 1500. The treatment applied an average of 15 kilovolts energy per pulse with the minimum being 14 kilovolts and the maximum 16 kilovolts. Treatment included a local or plexus anesthesia. The side effects included petechial bleedings and post-treatment pain, both of which subsided rapidly.

As explained above, each of the patients chosen for this study did not respond to conventional therapy. Of the total number of patients treated using acoustic shock wave therapy for epicondylitis, the average time for conventional treatment period was 13 months with no response. The maximum prior conventional prior treatment period was 48 months. The minimum prior treatment period for the group of patients was 4 months. Each patient received the acoustic shock wave therapy on an outpatient basis, and follow up examinations after 3–6 months for each patient yielded no reoccurrence of the condition.

EXAMPLE 3

This study included treatment for 131 patients suffering from pseudarthrosis, which is a condition wherein a new, false joint arises at the site of a non-united fracture, as illustrated in Table 3.

TABLE 3

Preliminary Clinical Results For Treatment of Pseudarthrosis Using Acoustic Shock Waves

| | | |
|---|---|---|
| Number of patients: | | 131 |
| Success Rate: | total | 77% |
| | single treatment: | 57% |
| | double treatment: | 20% |
| Shocks Per Treatment: | average: | 2450 |
| | min: | 800 |
| | max: | 4000 |
| Energy Per Pulse: | average: | 24 kV |
| | min: | 18 kV |
| | max: | 28 kV |
| Pulse Frequency: | average: | 0.5–4.0 Hz |
| Treatment Duration | average: | 30–40 minutes |
| Anesthesia: | general, spinal, peridural, local | |
| Side Effects: | petechial bleedings, local swelling | |
| History: | Time of prior conventional therapies: | |
| | average: 23 months | |
| | min: 4 months | |
| | max: 20 years | |
| | Prior treatment: One or multiple surgeries, including osteosynthesis | |
| | Hospitalization: usually outpatient | |
| | Follow-up: 3–6 months | |

This study included 131 patients treated with an average success rate of 77%. The average success rate consisted of a sum of 57% of the treated patients receiving a single treatment and 20% of the treated patients receiving a double treatment. The treatment employed an average number of shocks applied per session of 2450, with the minimum being 800 and the maximum being 4000. The treatment applied an average of 24 kilovolts energy per pulse with the minimum being 18 kilovolts and the maximum 28 kilovolts. Treatment included one or more of the following types of anesthesia: general, spinal, peridural, and local. The side effects included petechial bleedings and local swelling, both of which dissipated rapidly.

As explained above, each of the patients chosen for this study did not respond to conventional treatment for fracture and faced further surgery, bone grafting, etc. Of the total number of patients treated using acoustic shock wave therapy for pseudarthrosis, the average time after fracture was 13 months. The maximum time period from fracture was 20 years. The minimum time period from fracture was 4 months. Prior treatment for this group of patients included one or multiple surgeries including osteosynthetic procedures. Each patient received the acoustic shock wave therapy on an outpatient basis or over a 2–3 day hospital visit, and follow up examinations after 3–6 months for each patient yielded no recurrence of the condition.

Table 4 below summarizes the technical parameters of methods for using acoustic shock waves in the treatment of some medical conditions.

TABLE 4

Summary of Technical Parameters of Various Acoustic Shock Wave Treatment Parameters

| | Calcific Tendinitis | Epicondylitis | Pseudarthrosis | Plantar Fasciitis |
|---|---|---|---|---|
| Frequency of shock wave impact | 0.5–4.0 Hz @ fixed frequency | 0.5–4.0 Hz @ fixed frequency | 0.5–4.0 Hz @ fixed frequency | 0.5–4.0 Hz @ fixed frequency |
| Pulse duration | average rise time 33 ns; average pulse width 280 ns | average rise time 33 ns; average pulse width 280 ns | average rise time 33 ns; average pulse width 280 ns | average rise time 33 ns; average pulse width 280 ns |
| Treatment period (minutes) | as needed to identify treatment site and deliver up to 2500 pulses, approx. 20–30 min | as needed to identify treatment site and deliver up to 1500 pulses, approx. 20–30 min | as needed to identify treatment site(s) and deliver from 1000 to 8000 pulses, approx. 45–60 min | as needed to identify treatment site and deliver up to 1000 pulses, approx. 20–30 min |
| Posttreatment care | return to normal activities | return to normal activities | recast and treat as fresh fracture | return to normal activities |
| Tissue type at focal point | tendons of shoulder joint at the insertion into bone | tendons of the elbow joint at the intersection into bone | fractured bone that has delayed or failed to heal | fascia of the heel at the insertion into bone |
| Types of ineffective conventional therapy | application of heat, ice physical therapy Non-steroidal anti-inflammatory drugs (NSAIDs) Steroid injection Surgical Intervention | application of heat, ice physical therapy Non-steroidal anti-inflammatory drugs (NSAIDs) Steroid injection Surgical Intervention | dynamic internal or external fixation immobilization surgical debridement electrical/electromagnetic bone growth stimulator | application of heat, ice physical therapy Non-steroidal anti-inflammatory drugs (NSAIDs) Steroid injection Surgical Intervention |

While the examples and tables above focus on the treatment of four selected pathological conditions, acoustic shock wave therapy is further applicable to a wide range of pathological conditions. Certain exemplary embodiments of the invention may include a wide range in the various parameters used to treat all of the pathologies mentioned in this specification. Specifically, for each of the pathologies mentioned in this specification, an exemplary embodiment of the invention may include applying a range of approximately 14–28 kilovolts of energy per pulse; the pulse frequency may be approximately 0.5–4 Hz (pulses/sec), and the pulse duration may be approximately 280 ns. The number of pulses per treatment should be approximately 500–8,000, and the total time per treatment should be approximately 20 minutes to 3 hours. The total energy per treatment may be from 2500 to 150,000 mJ. Additionally, the number of treatments necessary for a positive response may vary from 1 to 3 for each pathology discussed below. For all of the pathological conditions below, there is typically an increasing benefit for additional treatments, with most indications requiring an average of 1.5 treatments.

Although the several methods of shock wave generation and various physical parameters have been discussed above, a brief discussion of various energy parameters used by those skilled in the art may also be helpful. For more detailed information than that provided below, the reader is referred to the publication entitled "Principles of Shock Wave Therapy" by John A. Ogden, M. D. et al. in *Clinical Orthopaedics and Related Research*, No. 387, pp. 8–17, said publication being incorporated herein by reference in its entirety.

Energy flux density is a measure of the energy per square area that is being released by the sonic pulse at a specific, finite point. Energy flux density may be derived from pressure and can be computed as the area below the squared pressure time curve. The pressure (typically measured in MPa) generated by a shock wave as a function of time and space is the parameter that is most amenable to direct measurement. The pressure field is maximal at the focal center, but in addition, significant effects may be produced over neighboring regions of tissue and the dimensions of such zones will vary according to the precise shock wave treatment provided. The zone around the focal region may be defined in three different axes to create the focal volume.

Energy flux density should not be confused with energy. The energy flux (as much as 1.5 mJ/mm$^2$) and the peak pulse energy (as many as 100 MPa) are determined by the temporal and spatial distribution of the pressure profile. The energy flux density describes the maximum amount of acoustical energy that is transmitted through an area of 1 mm$^2$ per pulse. The total pulse energy is the sum of all energy densities across the beam profile and describes the total acoustical energy per released shock wave. Although energy flux density relates to the energy released at a certain point, the energy of a shock wave is the total amount of energy released within a defined region.

The total energy applied to the tissue is represented by the number of pulses multiplied by the energy per pulse. Theoretically, pressure and energy are concentrated within a point, the focus. The treatment focus has finite dimensions. The pressure is highest in the focal center and decreases with increasing distance from the focus. According to ultrasound physics, the focal regions of a shock wave may be defined by three different conditions: the 5 mm area, the 6 dB area, and the 5 MPa area. The 5 mm area is simply a sphere surrounding the treatment focal point whose radius is 5 mm. The 6 dB area may be defined as the volume of tissue in millimeters within which the pressure is at least half its peak value. The 5 MPa area may be defined in a similar fashion as the volume of tissue defined in millimeters along x, y, and z axes within which the pressure exceeds 5 MPa.

The volume within these defined boundaries should be assessed for the maximum, minimum, and intermediate energy settings of any relevant shock wave device. The physical parameters of positive peak pressure and the various zones in the clinically sensitive −6 dB focal areas for high-, medium-, and low-energy devices is available from the International Society for Musculoskeletal Shock Wave Therapy (www.ismst.com). Measurements have been completed using unified standards, and the individual values of the various devices on the market (especially in Europe) or being tested (in the United States) are published by the German and International Society for Extracorporeal Shock Wave Therapy (www.shockwavetherapy.net). An exemplary shock wave device is the Ossatron®, which is manufactured by HMT High Technologies AG of Lengwil, Switzerland. The physical parameters of the Ossatron® are reproduced in Table 5 below:

TABLE 5

| Voltage (kV) | Pressure (MPa) | Energy flux density (mJ/mm$^2$) | Energy-6 dB (mJ) | Energy-5 mm (mJ) | Energy-5 MPa (mJ) | Focal extend in x, y direction (−6 dB) | Focal extend in z direction (−6 dB) |
|---|---|---|---|---|---|---|---|
| 14 | 40.6 | 0.12 | 4.9 | 2.9 | 22.2 | 6.8 | 44.1 |
| 15 | 40.9 | 0.14 | 4.9 | 3.3 | 22.5 | 6.7 | 48 |
| 16 | 41.3 | 0.17 | 4.9 | 3.9 | 23.4 | 6.7 | 51 |
| 17 | 42 | 0.19 | 5 | 4.4 | 24.9 | 6.7 | 53.5 |
| 18 | 42.9 | 0.22 | 5 | 4.9 | 27.2 | 6.7 | 55.6 |
| 19 | 44.1 | 0.25 | 5 | 5.5 | 30.2 | 6.7 | 57.4 |
| 20 | 45.6 | 0.27 | 5.1 | 5.8 | 34.2 | 6.4 | 59 |
| 21 | 47.4 | 0.29 | 6.2 | 6.5 | 39.2 | 6.8 | 60.4 |
| 22 | 49.6 | 0.32 | 7.7 | 7.1 | 45.3 | 6.9 | 61.7 |
| 23 | 52.2 | 0.34 | 9.7 | 7.6 | 52.6 | 7.1 | 62.9 |
| 24 | 55.2 | 0.36 | 12.2 | 8.2 | 61.1 | 7.3 | 64 |
| 25 | 58.7 | 0.37 | 15.2 | 8.7 | 71.1 | 7.6 | 65 |
| 26 | 62.6 | 0.38 | 18.8 | 9.2 | 82.5 | 7.9 | 65.9 |
| 27 | 67 | 0.39 | 23.1 | 9.8 | 95.5 | 8.3 | 66.8 |
| 28 | 71.9 | 0.4 | 28 | 10.4 | 110.2 | 8.7 | 67.9 |

It should be understood that embodiments of this invention are not limited to embodiments utilizing the Ossatron® or the other systems and devices described above for generating, focusing, and/or applying acoustic shock waves.

A certain threshold value of energy density has to be exceeded to stimulate any healing process, and to lead to any significant side effects. Such a threshold dosage of energy is not different from concepts such as bacteriocidal and bacteriostatic effects of an antibiotic. Although the energy density (mm$^2$/mJ) of a shock wave is important, the more clinically relevant physical parameter may be the total amount of acoustic energy administered in a single shock wave treatment.

An embodiment according to the present invention may accelerate the healing of pathologic cutaneous, subcutaneous, and fascial geographic tissue injuries, defects, and deficits, such as diabetic foot ulcers or pressure sores. Application of acoustic shock waves disrupts the thick necrotic tissue, causing breakdown, which then enhances revascularization of the pathologic tissues, creating a granulomatous base that allows for progressive migration and maturation of dermal and epidermal tissues. Furthermore, the acoustic shock waves may disrupt the capsules of infecting bacteria, enhancing the uptake of antibiotics. Such an acoustic shock wave treatment should apply an average of approximately 14–26 kilovolts, more preferably 20–26 kV, of energy per pulse. The pulse frequency should be approximately 0.5–4.0 Hz and the pulse duration should be approximately 280 ns. The number of pulses per treatment may be more than 500 to about 2500, and a range of more than 1000 to about 2500 is more preferable. The total time per treatment should be in the range of approximately 20 to 60 minutes, and the total energy per treatment should be about 2500 to about 12,500 mJ.

An embodiment according to the present invention may also be used to treat arthritis and other degenerative joint diseases, including rheumatoid arthritis, osteoporosis, and osteomalacia. The treatment for those conditions should include an average number of shocks applied per session of about 500 to about 2500. The treatment should apply an average of approximately 14–28 kilovolts of energy per pulse. The pulse frequency should be approximately 0.5–4.0 Hz, and the pulse duration should be approximately 280 ns. The total time per treatment should be in the range of approximately 20 to 45 minutes, and the total energy per treatment should be about 5000 to about 15,000 mJ.

Acoustic shock waves may also be used to accelerate the rate of healing of soft tissue injuries, such as damaged rotator cuffs. Such a treatment should apply an average of approximately 14–28 kilovolts of energy per pulse. The pulse frequency should be approximately 0.5–4.0 Hz, and the pulse duration should be approximately 280 ns. The number of pulses per treatment should be about 500 to about 2500, and the total time per treatment should be in the range of approximately 20 to 45 minutes. The total energy per treatment should be about 2500 to about 15,000 mJ.

The reabsorption of impending heterotopic calcifications and ossifications may also be accelerated by application of an exemplary embodiment of a method according to the present invention. Focusing acoustic shock waves on the site associated with the impending heterotopic calcification or ossification fragments the impending heterotopic calcification or ossification microscopically, thereby accelerating healing. In particular, the surrounding shell and fibrotic capsule protecting the calcification or ossification from the reabsorption process would be destroyed or damaged. Such a treatment should apply an average of approximately 14–28 kilovolts of energy per pulse. The pulse frequency should be approximately 0.5–4.0 Hz, and the pulse duration should be approximately 280 ns. The number of pulses per treatment should be about 1000 to about 4000, and the total time per treatment should be in the range of 20 minutes to 1 hour. The total energy per treatment should be about 28,000 to about 115,000 mJ.

An exemplary embodiment of the invention may be used to treat sacroiliac pain, wherein the acoustic shock waves are focused between the sacrum and pelvic bone surface (ilium). Such a treatment should apply an average of approximately 14–28 kilovolts of energy per pulse. The pulse frequency should be approximately 0.5–4.0 Hz, and the pulse duration should be approximately 280 ns. The number of pulses per treatment should be about 1500 to about 4000, and the total time per treatment should be in the range of approximately 40 to 90 minutes. The total energy per treatment should be about 32,000 to about 115,000 mJ.

An exemplary embodiment of the invention may be used to treat osteochondromatosis and enchondromatosis (tumors of the growth plate), as well as facet osteoarthritis. Applying a sufficient number of acoustic shock waves induces micro-injury and increased vascularization in order to slow or stop abnormal activity of the genetically altered growth cartilage associated with osteochondromatosis or enchondromatosis. Treatment generally involves applying an average of approximately 14–28 kilovolts of energy per pulse. The pulse frequency should be approximately 0.5–4.0 Hz, and the pulse duration should be approximately 280 ns. The number of pulses per treatment should be about 1000 to about 5000, and the total time per treatment should be in the range of approximately 20 to 150 minutes. The total energy per treatment should be about 28,000 mJ to about 140,000 mJ.

Examples of additional pathological conditions which respond positively to certain exemplary embodiments of the present invention include focal reflex dystrophy pain, phantom pain, and focal pain due to an abnormal enlargement of a nerve (such as a neuroma). Treatments for these pathological conditions generally involve applying an average of approximately 14–28 kilovolts of energy per pulse. The pulse frequency should be approximately 0.5–4.0 Hz, and the pulse duration should be approximately 280 ns. The number of pulses per treatment should be about 1000 to about 5000, and the total time per treatment should be in the range of approximately 20 to 150 minutes. The total energy per treatment should be about 3000 to about 10,000 mJ.

Other exemplary embodiments of the invention may promote stimulation of bone formation and vascular ingrowth in bone lengthening, fusion in partially ankylosed joints, and selective partial or complete closure of growth cartilage in cases of bone length inequality or angular deformity. Treatments for these pathologies should apply an average of approximately 14–28 kilovolts of energy per pulse. The pulse frequency should be approximately 0.5–4.0 Hz, and the pulse duration should be approximately 280 ns. The number of pulses per treatment should be about 1000 to about 5000, and the total time per treatment should be in the range of approximately 20 to 150 minutes. The total energy per treatment should be about 28,000 to about 140,000 mJ.

An exemplary embodiment according to the invention may be used to treat repetitive motion injuries including carpal tunnel and tarsal tunnel syndromes. Such a treatment should apply an average of approximately 14–28 kilovolts of energy per pulse. The pulse frequency should be approximately 0.5 to 4.0 Hz, and the pulse duration should be approximately 280 ns. The number of pulses per treatment should be approximately 500–2500, and the total time per treatment should be in the range of approximately 20 minutes to 45 minutes. The total energy per treatment should be about 5000 to about 15,000 mJ.

The bone density and extent of calcification in osteoporotic sites can be increased according to an embodiment of the present invention. The effects of the focused acoustic waves on osteoporotic sites can be prolonged and maintained indefinitely when used in conjunction with drugs such as Fosamax™. For example, an osteoporotic wrist requires a treatment having an average of approximately 14–28 kilovolts of energy per pulse. The pulse frequency should be approximately 0.5 to 4.0 Hz and the pulse duration should be approximately 280 ns. The number of pulses per treatment should be approximately 800–4000, the total time per treatment should be in the range of approximately 30 minutes to 1 hour and 30 minutes, and the total energy per treatment should be about 28,000 to about 140,000 mJ. The inventive treatment is also effective on other osteoporotic sites. However, the number of pulses per treatment must increase with increasing bone mass. For example, an osteoporotic hip may require up to 8,000 shocks in a single treatment.

Acoustic shock waves may be used to enhance bone formation and remodeling in stress fractures. Such a treatment should apply an average of approximately 14–28 kilovolts of energy per pulse. The pulse frequency should be approximately 0.5–4.0 Hz, and the pulse duration should be approximately 280 ns. The number of pulses per treatment should be approximately 1000–8000, and the total time per treatment should be in the range of approximately 45 minutes to 2 hours. The total energy per treatment should be about 28,000 to about 140,000 mJ.

Non-adaptive bone diseases in equines and canines may also be treated using acoustic shock waves. For example, to the extent that all of the above-referenced pathological conditions occur in equines and canines, all of the above-referenced treatments are applicable to the treatment of equines, canines, or other animals.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A method of treating a diabetic foot ulcer or a pressure sore, comprising:
  locating a site or suspected site of the diabetic foot ulcer or pressure sore in a human patient;
  generating acoustic shock waves;
  focusing the acoustic shock waves throughout the located site; and
  applying more than 500 to about 2500 acoustic shock waves per treatment to the located site to induce micro-injury and increased vascularization thereby inducing or accelerating healing.

2. The method of claim 1, wherein more than 1000 acoustic shock waves are applied per treatment.

3. The method of claim 1, wherein generating acoustic shock waves comprises applying a voltage potential across a spark gap of a spark gap generator ranging from about 14 kV to about 26 kV to generate each shock wave.

4. The method of claim 1, wherein applying acoustic shock waves comprises applying the acoustic shock waves in a single treatment.

5. The method of claim 1, wherein a total energy applied to the located site per treatment is about 2,500 to about 12,500 mJ.

6. The method of claim 1, wherein more than 500 to about 1000 acoustic shock waves are applied per treatment.

7. The method of claim 1, wherein more than 1000 to about 2500 acoustic shock waves are applied per treatment.

8. The method of claim 1, wherein a total time per treatment is in a range of approximately 20 to 60 minutes.

9. The method of claim 1, wherein the acoustic shock waves disrupt capsules of infecting bacteria at the located site.

10. The method of claim 1, wherein the locating step includes locating a site or suspected site of the diabetic foot ulcer in the human patient.

11. The method of claim 1, wherein the locating step includes locating a site or suspected site of the pressure sore in the human patient.

* * * * *